United States Patent [19]
Wimmer

[11] Patent Number: 5,200,192
[45] Date of Patent: Apr. 6, 1993

[54] INSTANT ORAL-RELEASE CAPSULE CONTAINING NIFEDIPINE

[76] Inventor: Walter Wimmer, Blumenroder Strasse 68, 6250 Limburg/Lahn, Fed. Rep. of Germany

[21] Appl. No.: 270,957

[22] Filed: Nov. 14, 1988

[30] Foreign Application Priority Data

Nov. 11, 1987 [DE] Fed. Rep. of Germany ....... 3738236

[51] Int. Cl.$^5$ .............................................. A61K 9/65
[52] U.S. Cl. .................................... 424/455; 424/451; 424/456; 424/452
[58] Field of Search ............... 424/455, 456, 452, 451; 514/929, 962, 970, 972

[56] References Cited

U.S. PATENT DOCUMENTS

| | | | |
|---|---|---|---|
| 3,784,684 | 1/1974 | Bossert et al. ....................... | 424/455 |
| 4,689,233 | 8/1987 | Dvorsky et al. ..................... | 424/455 |
| 4,690,823 | 9/1987 | Lohner et al. ....................... | 424/455 |
| 4,695,450 | 9/1987 | Bauer et al. ......................... | 424/455 |
| 4,904,699 | 2/1990 | Bauer .............................. | 514/970 X |

Primary Examiner—Thurman K. Page
Assistant Examiner—Leon R. Horne
Attorney, Agent, or Firm—Christie, Parker & Hale

[57] ABSTRACT

The invention concerns an instant oral-release capsule containing an aqueous or aqueous alcoholic solution of nifedipine, containing a polyalkylene glycol and a polyoxyethylene ester component, the amount of the ester component in the solution being sufficient to prevent precipitation of nifedipine in the mouth of a patient after release of the solution from the capsule. Preferably, the ester component is an ethoxylated hydrogenated castor oil Cremophor RH40. The solution may further contain a second glycol component, especially glycerol.

23 Claims, 1 Drawing Sheet

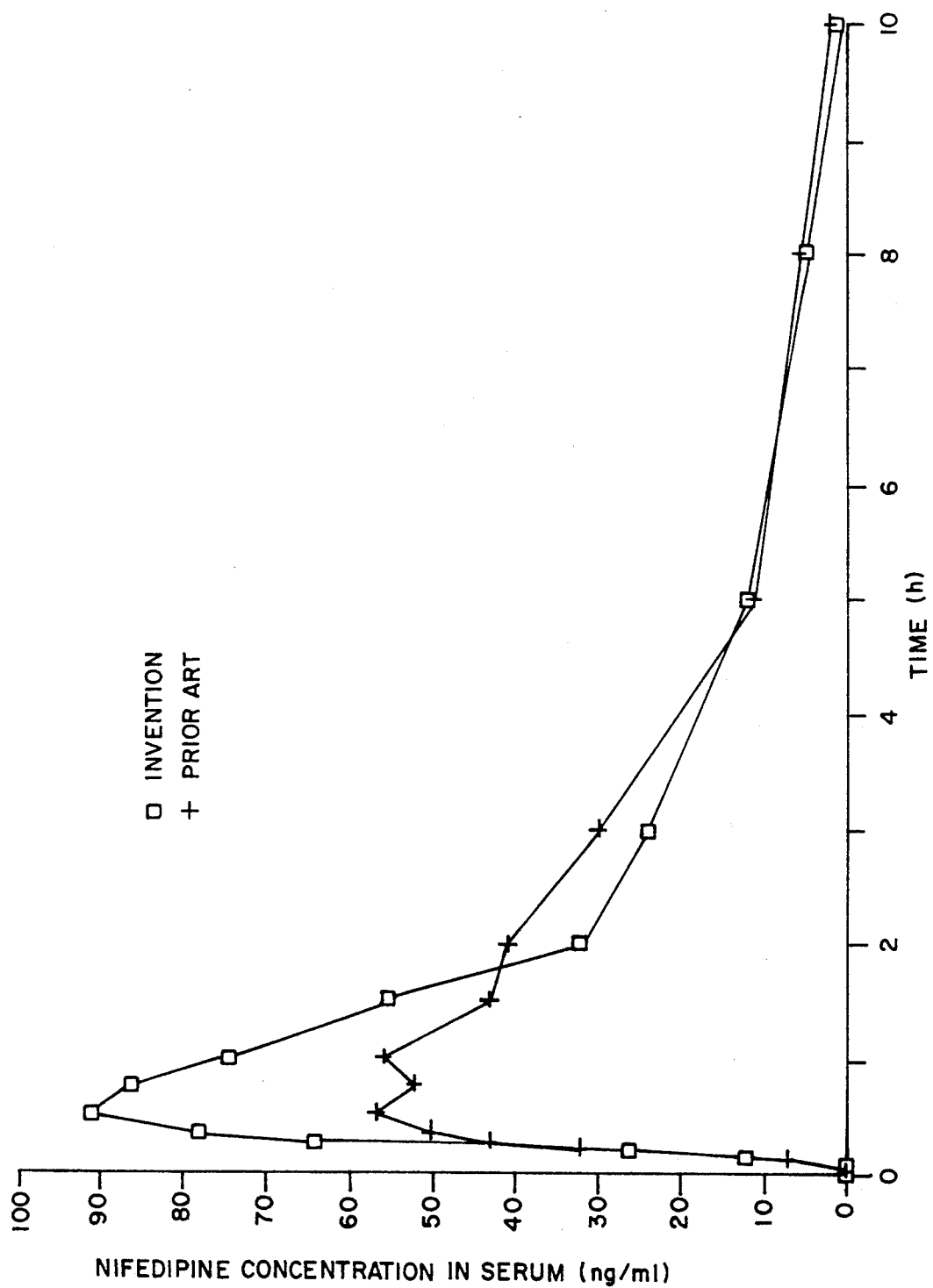

INSTANT ORAL-RELEASE CAPSULE CONTAINING NIFEDIPINE

DESCRIPTION

The invention concerns an instant oral-release capsule containing nifedipine in solution.

Pharmaceutical nifedipine preparations in the form of soft gelatin oral-release capsules are of major importance in the treatment of coronary diseases. When needed, a capsule is bitten by the patient, so that the solution is released from the capsule into the patient's mouth. Immediate action of the nifedipine is desired, so that the absorption of the capsule's nifedipine content by body tissues must be as fast as possible; on the other hand, the nifedipine must remain in the patient's body for the required duration.

The absorption of solid nifedipine by body tissue proceeds very slowly, so that solid nifedipine preparations are unsuitable for coronary therapeutical applications. The absorption of nifedipine from solutions is much faster.

Nifedipine dissolves in aqueous media only to a very small extent, so that aqueous solutions cannot provide the nifedipine concentrations required for therapeutical purposes. Nifedipine dissolves much better in polyalkylene glycols, especially upon moderate warming. In prior art, therefore polyalkylene glycol solutions of nifedipine have been used in an attempt to achieve the required bioavailability of nifedipine.

Such prior art capsules are known from DE 22 09 526. This patent discloses an oral-release capsule with a soft gelatin capsule body containing a solution of nifedipine in, substantially, a mixture of polyethylene glycol and glycerol. Such capsules have for years been marketed under the name "Adalat" (TM).

Yet these known capsules do not achieve instantaneous maximal bioavailability of nifedipine. One reason for this disadvantage appears to be the fact that nifedipine solubility decreases once the capsule solution is released from the capsule and mixed with aqueous body fluids, especially saliva. Part of the nifedipine is then precipitated from the solution, so that the absorption is slowed down, resulting in a delay in reaching the required nifedipine blood level.

For alternative nifedipine formulations, i.e. sublingual sprays, an attempt at overcoming related problems was described in EP 240 484. According to this prior art, a nifedipine spray solution should contain a combination of polyvinylpyrrolidone, copolyvidone, propylene carbonate and an emulsifier. The compositions disclosed in this prior art are not suitable for capsules. For several reasons, especially in view of the problems involved in administering exact nifedipine dosage amounts through spraying, nifedipine sprays are less advantageous than capsules.

It is therefore an object of the invention to provide an instant oral-release capsule capable of providing instantaneous maximal bioavailability of nifedipine.

It is a further object of the invention to provide such a capsule, achieving at the same time substantially the same duration of nifedipine bioavailability in the patient's body as provided by prior art capsules.

These and other technical objects and advantages are achieved by an instant oral-release capsule containing an aqueous or aqueous alcoholic solution of nifedipine, a polyalkylene glycol and a polyoxyethylene ester component, the amount of the polyoxyethylene ester component in the solution being sufficient to prevent precipitation of nifedipine in the mouth of a patient after release of the solution from the capsule.

The invention advantageously prevents nifedipine precipitation in the mouth of the patient, after the solution is released from the capsule and mixed with aqueous media such as saliva, gastro-intestinal fluids etc. This is probably largely due to the presence of the polyoxyethylene ester component in the solution, although it is assumed that synergistic effects are present, the polyalkylene glycol and water in the solution of the polyoxyethylene ester component.

The polyoxyethylene ester has hydrophilic and lipophilic groups, which are probably responsible for the precipitation-preventing effect. The ester component can thus be regarded as an emulsifier.

A variety of polyoxyethylene ester components are usable in the context of the invention, but of course they must be non-toxic and pharmaceutically acceptable. Preferably, the ester component should also be neutral in taste. Polyoxyethylene ester components usable in the context of the invention comprise ethoxylated glycerides, especially mono- or triglycerides; ethoxylated fatty acid esters; ethoxylated castor oil derivatives and mixtures of two or more of such substances.

It is especially advantageous to use ethoxylated hydrogenated castor oil products as the polyoxyethylene ester component; an especially preferred such product is commercially available under the name Cremophor RH40.

The amount of the polyoxyethylene ester component in the solution should be between about 3 and 33 weight percent and preferably about 7 to 15 weight percent of the solution. Chosing the most suitable concentration of the polyoxyethylene ester component in the solution is substantially a matter of compromise; higher contents of the ester component allow higher degrees of dilution with aqueous media, before precipitation of nifedipine sets in, but on the other hand such higher ester component contents increase the danger of the solution's taste being adversely affected. At the above-mentioned concentrations, taste is practically unimpaired, while no precipitation of nifedipine is observed under usual conditions, neither in the mouth nor in the gastro-intestinal tract.

The polyalkylene glycol component of the solution is preferably a polyethylene glycol (PEG). The PEG should have an average molecular weight smaller than 2000; presently, the PEG is most preferred to have an average molecular weight of about 400. The amount of the PEG or other polyalkylene glycol in the solution is preferably between about 50 and 90 weight percent. Presently most preferred is a PEG concentration in solution of about 70 to 85 weight percent.

While it is thus possible to use a solution containing (besides water, taste-improving substance if required and, of course, nifedipine) only PEG 400 and Cremophor RH40, especially in a 9 to 1 weight percent ratio, it is presently more preferred to further add a second glycol component to the solution, especially if this second glycol component is glycerol. The amount of this second glycol component, especially glycerol, in the solution can advantageously lie between about 2 and 15 weight percent, and most preferred at about 5 to 10 weight percent.

An instant oral-release capsule forming what is presently regarded as the best embodiment of this invention contains about 500 mg of solution, the solution containing about 10 mg nifedipine, about 403 mg polyethylene glycol with an average molecular weight of about 400, about 35 mg glycerol, about 41 mg ethoxylated hydrogenated castor oil Cremophor RH40 and about 9.5 mg water, about 1.5 mg peppermint oil and artificial sweetener being added as taste-improving substances. The capsule body is formed of soft gelatin and contains light-protective pigments, since nifedipine is highly light-sensitive. The capsule body of this embodiment weighs about 200 mg, so that the overall weight of the oral-release capsule is about 700 mg.

The invention will now be described in greater detail, comparing the effects achievable through the invention with those of the prior art capsules, similar to those disclosed in DE 22 09 526.

For the comparative tests to be described in detail hereinafter, instant oral-release capsules (A) according to the invention were prepared, which only slightly differ from the above-mentioned presently most preferred embodiment of the invention.

These capsules had a capsule body consisting of gelatin with a content of glycerol as a softening agent. The capsule body further contained light-protective pigments, namely titanium(IV)oxide, yellow iron oxide, red iron oxide and brown iron oxide. The capsule body further contained minor amounts of sodium benzoate salts. The overall weight of the capsule body was approximately 200 mg.

These capsule bodies were each filled with approximately 500 mg of solution. The solution contained 10 mg nifedipine, dissolved in a mixture of about 35 mg glycerol, about 370 mg PEG 400, about 41 mg Cremophor RH40, about 44 mg water and, as taste-improving substances about 1.5 mg peppermint oil and sweetener (saccharin sodium).

The overall weight of the oral-release capsule was thus approximately 700 mg.

When these capsules were administered to patients, no unpleasant taste was reported after the patients had bitten the capsules.

As a comparison, oral-release capsules (B) closely corresponding to the prior art capsules were prepared, using the same kind of capsule bodies as for the comparison capsules according to the invention.

These capsule bodies were again each filled with approximately 500 mg of solution. The solution contained 10 mg nifedipine, dissolved in a mixture of about 35 mg glycerol, about 409 mg PEG 400, about 44 mg water and about 2 mg peppermint oil and saccharin sodium as taste-improving substances.

The overall weight of these oral-release capsules was thus also approximately 700 mg.

Both kinds of capsules, those according to the invention and those corresponding to prior art, were used in a clinical cross-over study.

For this study, 5 patients were chosen, the personal data of which are given in table I.

TABLE I

| Patient | Height (cm) | Weight (kg) | Age (a) | Sex | Appln Sequence | Smoker |
|---|---|---|---|---|---|---|
| 1 KLH | 177 | 72 | 39 | m | B/A | + |
| 2 KUJ | 177 | 70 | 21 | m | A/B | + |
| 3 LOG | 176 | 60 | 31 | m | B/A | + |
| 4 NAG | 175 | 76 | 29 | m | B/A | − |
| 5 ROL | 178 | 70 | 25 | m | A/B | + |
| Mean: | 176.6 | 69.6 | 29.0 | | | |
| SDev: | 1.1 | 5.9 | 6.8 | | | |

TABLE I-continued

| Patient | Height (cm) | Weight (kg) | Age (a) | Sex | Appln Sequence | Smoker |
|---|---|---|---|---|---|---|
| CV: | .01 | .08 | .23 | | | |

The capsules were administered orally; the mouth cavities of all patients were normal. In Table I and the following tables, A represents the capsules according to the invention, while B represents the prior art capsules.

Table II contains data for nifedipine concentration in serum (ng/ml) after administration of capsules A.

TABLE II

| | Patient | | | | | | | |
|---|---|---|---|---|---|---|---|---|
| Time | 1 | 2 | 3 | 4 | 5 | Mean | SDev | CV |
| 00:00 | 0 | 0 | 0 | 0 | 0 | 0 | 0 | 0.000 |
| 00:04 | 0 | 0 | 0 | 0 | 0 | 0 | 0 | 0.000 |
| 00:08 | 6 | 9 | 7 | 26 | 12 | 12 | 8 | 0.671 |
| 00:12 | 19 | 39 | 11 | 53 | 8 | 26 | 19 | 0.733 |
| 00:16 | 35 | 118 | 33 | 117 | 19 | 64 | 49 | 0.757 |
| 00:20 | 55 | 121 | 61 | 124 | 31 | 78 | 42 | 0.532 |
| 00:30 | 90 | 102 | 47 | 130 | 86 | 91 | 30 | 0.329 |
| 00:45 | 78 | 85 | 44 | 105 | 116 | 86 | 28 | 0.326 |
| 01:00 | 60 | 69 | 40 | 68 | 132 | 74 | 35 | 0.467 |
| 01:30 | 49 | 66 | 28 | 53 | 78 | 55 | 19 | 0.338 |
| 02:00 | 25 | 41 | 24 | 35 | 37 | 32 | 8 | 0.236 |
| 03:00 | 23 | 27 | 13 | 20 | 37 | 24 | 9 | 0.377 |
| 05:00 | 12 | 10 | 5 | 7 | 23 | 12 | 7 | 0.603 |
| 08:00 | 8 | 2 | 0 | 4 | 10 | 5 | 4 | 0.879 |
| 10:00 | 0 | 0 | 0 | 0 | 6 | 1 | 3 | 2.236 |

Table III shows the comparison data of nifedipine concentration in serum (ng/ml) after administration of capsules B.

TABLE III

| | Patient | | | | | | | |
|---|---|---|---|---|---|---|---|---|
| Time | 1 | 2 | 3 | 4 | 5 | Mean | SDev | CV |
| 00:00 | 0 | 0 | 0 | 0 | 0 | 0 | 0 | 0.000 |
| 00:04 | 0 | 0 | 0 | 0 | 0 | 0 | 0 | 0.000 |
| 00:08 | 2 | 0 | 5 | 7 | 21 | 7 | 8 | 1.155 |
| 00:12 | 6 | 7 | 6 | 14 | 127 | 32 | 53 | 1.675 |
| 00:16 | 8 | 16 | 10 | 22 | 160 | 43 | 66 | 1.516 |
| 00:20 | 11 | 24 | 15 | 31 | 167 | 50 | 66 | 1.330 |
| 00:30 | 26 | 43 | 24 | 45 | 146 | 57 | 51 | 0.890 |
| 00:45 | 22 | 32 | 38 | 49 | 121 | 52 | 40 | 0.760 |
| 01:00 | 24 | 33 | 65 | 46 | 111 | 56 | 35 | 0.623 |
| 01:30 | 33 | 30 | 39 | 29 | 83 | 43 | 23 | 0.529 |
| 02:00 | 40 | 64 | 25 | 25 | 53 | 41 | 17 | 0.412 |
| 03:00 | 21 | 30 | 18 | 44 | 36 | 30 | 11 | 0.364 |
| 05:00 | 11 | 13 | 5 | 11 | 17 | 11 | 4 | 0.387 |
| 08:00 | 5 | 7 | 0 | 9 | 9 | 6 | 4 | 0.620 |
| 10:00 | 0 | 0 | 0 | 3 | 5 | 2 | 2 | 1.421 |

BRIEF DESCRIPTION OF THE DRAWING

In FIG. 1 the average values of nifedipine serum concentration data for capsules A and B are compared for all patients.

Table IV lists the areas under the curves (ng/mlxh) for $AUC_{0-10}$.

TABLE IV

| Patient | A | B |
|---|---|---|
| 1 | 198.7 | 139.8 |
| 2 | 228.4 | 190.2 |
| 3 | 109.8 | 119.1 |
| 4 | 216.5 | 199.9 |
| 5 | 314.3 | 346.4 |
| Mean | 213.5 | 199.1 |
| SDev | 73.1 | 89.0 |
| CV | 0.342 | 0.447 |

Table V lists the areas under the curves (ng/mlxh) for $AUC_{0-\infty}$.

TABLE V

| Patient | A | B |
|---|---|---|
| 1 | 225.3 | 153.0 |
| 2 | 230.5 | 207.3 |
| 3 | 112.0 | 120.8 |
| 4 | 223.5 | 213.2 |
| 5 | 338.9 | 366.0 |
| Mean | 226.1 | 212.1 |
| SDev | 80.3 | 94.2 |
| CV | 0.355 | 0.444 |

Table VI lists the concentration maxima (ng/ml).

TABLE VI

| Patient | A | B |
|---|---|---|
| 1 | 89.8 | 40.4 |
| 2 | 121.0 | 63.5 |
| 3 | 60.9 | 64.7 |
| 4 | 130.0 | 49.2 |
| 5 | 132.0 | 167.0 |
| Mean | 106.7 | 77.0 |
| SDev | 30.7 | 51.3 |
| CV | 0.288 | 0.667 |

Table VII lists the time durations (h) for attaining the maxima of table VI.

TABLE VII

| Patient | A | B |
|---|---|---|
| 1 | 0.50 | 2.00 |
| 2 | 0.33 | 2.00 |
| 3 | 0.33 | 1.00 |
| 4 | 0.50 | 0.75 |
| 5 | 1.00 | 0.33 |
| Mean | 0.53 | 1.22 |
| SDev | 0.27 | 0.75 |
| CV | 0.513 | 0.619 |

Table VIII lists the time durations (h) for attaining a serum concentration of 15 ng/ml ($t_{MEC}$).

TABLE VIII

| Patient | A | B |
|---|---|---|
| 1 | 0.179 | 0.378 |
| 2 | 0.147 | 0.258 |
| 3 | 0.212 | 0.330 |
| 4 | 0.105 | 0.206 |
| 5 | 0.241 | 0.115 |
| Mean | 0.177 | 0.258 |
| SDev | 0.053 | 0.103 |
| CV | 0.302 | 0.401 |

Table IX lists the elimination constants ($h^{-1}$).

TABLE IX

| Patient | A | B |
|---|---|---|
| 1 | 0.220 | 0.278 |
| 2 | 0.506 | 0.287 |
| 3 | 0.517 | 0.543 |
| 4 | 0.337 | 0.240 |
| 5 | 0.258 | 0.251 |
| Mean | 0.367 | 0.320 |
| SDev | 0.138 | 0.126 |
| CV | 0.376 | 0.394 |

The average terminal half-time for capsules A (invention) results as 1.89 h, while the average terminal half-time for capsules B (prior art) is 2.17 h.

As the data show, the required bioavailability levels are reached significantly faster upon administration of capsules A according to the invention.

Since in the practical use of nifedipine preparations, it is of the utmost importance to attain the required degree of bioavailability as fast as possible, the advantages provided by the invention are clear.

I claim:

1. An instant oral-release capsule comprising a capsule body formed of a soft gelatine containing a light protective pigment, said capsule containing an aqueous or aqueous alcoholic solution of nifedipine, a polyalkylene glycol and a polyoxyethylene ester component, the amount of the polyoxyethylene ester component in the solution being sufficient to prevent precipitation of nifedipine in the mouth of a patient after release of the 2. A capsule as claimed in claim 1 in which the polyoxyethylene ester component comprising a compound selected from the group consisting of an ethoxylated glyceride, an ethoxylated mono glyceride an ethoxylated triglyceride, an ethoxylated fatty acid ester, and an ethoxylated castor oil derivative, and mixtures thereof.

3. A capsule as claimed in claim 2 in which the polyoxyethylene ester component comprises an ethoxylated hydrogenated castor oil.

4. A capsule as claimed in claim 1 in which the solution contains between about 3 and 33 weight percent of the polyoxyethylene ester component.

5. A capsule as claimed in claim 1 in which the polyalkylene glycol is polyethylene glycol.

6. A capsule as claimed in claim 5 in which the polyethylene glycol has an average molecular weight less than 2000.

7. A capsule as claimed in claim 6 in which the polyethylene glycol has an average molecular weight of about 400.

8. A capsule as claimed in claim 1 in which the amount of the polyalkylene glycol in solution is between about 50 and 90 weight percent.

9. A capsule as claimed in claim 1 in which the solution further containing a second glycol component.

10. A capsule as claimed in claim 9 in which the second glycol component is glycerol.

11. A capsule as claimed in claim 9 in which the amount of the second glycol component in the solution is between about 2 and 15 weight percent.

12. A capsule as claimed in claim 1 in which the capsule containing about 500 mg of solution, the solution containing about 10 mg nifedipine, about 403 mg polyethylene glycol having an average molecular weight of about 400, about 35 mg glycerol, about 41 mg ethoxylated hydrogenated castor oil, about 9.5 mg water and about 1.5 mg of a flavoring substance.

13. A capsule as claimed in claim 3 in which the solution contains between about 3 and 33 weight percent of the polyoxyethylene ester component.

14. A capsule as claimed in claim 3 in which the solution contains between about 3 and 33 weight percent of the polyoxyethylene ester component.

15. A capsule as claimed in claim 2 in which the polyalkylene glycol is polyethylene glycol.

16. A capsule as claimed in claim 4 in which the polyalkylene glycol is polyethylene glycol.

17. A capsule as claimed in claim 15 in which the polyethylene glycol has an average molecular weight less than 400.

18. A capsule as claimed in claim 2 in which the polyethylene glycol has an average molecular weight less than 2000.

19. A capsule as claimed in claim 8 in which the polyalkylene glycol is present in an amount of from 70 to 85% by weight of the solution.

20. A capsule as claimed in claim 10 in which the second glycol component in the solution is present in an amount of from about 5 to 10% by weight of the solution.

21. A capsule as claimed in claim 10 in which the polyalkylene glycol component is present is an amount of from 70 to 85 weight percent of the solution.

22. A capsule as claimed in claim 7 in which the polyalkylene glycol component is present in an amount of from 70 to 85 weight percent of the solution.

23. A capsule as claimed in claim 20 in which the polyalkylene glycol component is present in an amount of from 70 to 85 weight percent of the solution.

* * * * *

UNITED STATES PATENT AND TRADEMARK OFFICE
CERTIFICATE OF CORRECTION

PATENT NO. : 5,200,192
DATED : April 6, 1993
INVENTOR(S) : Walter Wimmer

It is certified that error appears in the above-identified patent and that said Letters Patent is hereby corrected as shown below:

```
Column 2, line 29, after "preferred" delete 'such".
Column 2, line 29, before "commercially" delete "is".
Column 2, line 34, change "Chosing" to -- Choosing --.
Column 2, line 65, change "most preferred" to
                   -- preferably --.

Column 6, line 13, after "release of the" insert
                   -- solution from the capsule. --.
Column 6, line 18, after "glyceride" insert a comma.
Column 6, line 39, change "containing" to -- contains --.
Column 6, line 52, change "claim 3" to -- claim 2 --.

Column 8, line 2, after "present" change "is" to -- in --.
```

Signed and Sealed this

Thirty-first Day of May, 1994

*Attest:*

BRUCE LEHMAN

*Attesting Officer*     Commissioner of Patents and Trademarks